United States Patent [19]

Sewell, Jr.

[11] Patent Number: 5,364,406
[45] Date of Patent: Nov. 15, 1994

[54] LAPAROSCOPIC SURGICAL STAPLE

[76] Inventor: Frank Sewell, Jr., 1413 North Elm, Henderson, Ky. 42420

[21] Appl. No.: 107,271

[22] Filed: Aug. 16, 1993

Related U.S. Application Data

[62] Division of Ser. No. 734,246, Jul. 22, 1991, Pat. No. 5,236,435.

[51] Int. Cl.5 ............................................. A61B 17/04
[52] U.S. Cl. .................................. 606/138; 606/219; 128/898
[58] Field of Search .................... 606/219, 220, 138; 411/457, 473, 483, 920, 921; 227/19; 128/898

[56] References Cited

U.S. PATENT DOCUMENTS

| | | | |
|---|---|---|---|
| 249,851 | 11/1881 | McGill | 411/483 |
| 350,507 | 10/1886 | Schulz | 411/457 |
| 366,555 | 7/1887 | Brewington | 411/483 |
| 569,648 | 10/1896 | Logan | 411/457 |
| 733,679 | 7/1903 | Rupert | 411/473 |
| 2,530,811 | 11/1950 | Cook | 411/920 |
| 3,339,448 | 6/1967 | McKee | 411/473 |
| 3,372,477 | 3/1968 | Hoppe | 606/138 |
| 3,583,663 | 6/1971 | Snow | 411/457 |
| 3,643,851 | 2/1972 | Green et al. | 227/18 |
| 3,817,294 | 2/1973 | Green | 227/19 |
| 3,837,555 | 9/1974 | Green | 227/130 |
| 4,014,492 | 3/1977 | Rothfuss | 227/19 |
| 4,026,520 | 5/1977 | Rothfuss et al. | 254/28 |
| 4,073,179 | 2/1978 | Hickey et al. | 606/138 |
| 4,434,796 | 3/1984 | Karapetian et al. | 128/335 |
| 4,487,394 | 12/1984 | Rothfuss et al. | 254/28 |
| 4,515,348 | 5/1985 | Blake | 606/138 |
| 4,685,460 | 8/1987 | Thornton | 606/138 |
| 4,802,478 | 2/1989 | Powell | 606/138 |
| 4,805,876 | 2/1989 | Blake et al. | 254/28 |

Primary Examiner—Stephen C. Pellegrino
Assistant Examiner—Gary Jackson
Attorney, Agent, or Firm—Ice Miller Donadio & Ryan

[57] ABSTRACT

A laparoscopic surgical staple system comprises a staple, a staple extractor, and methods of applying and extracting such staples. The staples of the present invention are visible through a limited viewport, such as a trocar, and include an extraction member which forms a substantially closed hole through which a hook can be inserted. The staple extractor of the present invention includes a mechanism for grasping and pulling to remove the staple from body tissue, and a hook which can receive and hold multiple staples. The staples are applied by a device which is capable of inserting the staple's legs into a patient's body tissue. Staples are extracted using methods which allow multiple staples to be removed in a single, quick laparoscopic procedure and which reduce the risk of infection to the patient.

13 Claims, 5 Drawing Sheets

LAPAROSCOPIC SURGICAL STAPLE

CROSS REFERENCE TO RELATED APPLICATIONS

This is a division of application Ser. No. 07/734,246 filed Jul. 22, 1991, now U.S. Pat. No. 5,236,435.

FIELD OF THE INVENTION

This invention relates to a surgical stapling system, and, in particular, to a surgical staple, a staple extracting device, and methods of applying and extracting staples to be used in laparoscopic surgery.

BACKGROUND OF THE INVENTION

Laparoscopic surgery is an increasingly popular form of surgery. In laparoscopic surgery, several small incisions are made in the patient's abdomen and a tube, or trocar, is inserted through each incision. All surgical instruments, including staple or clip applicators and extractors, are inserted through a trocar. Although surgical staple applicators are capable of holding and applying multiple staples during a single insertion through a trocar, surgical staple extractors, such as those disclosed in U.S. Pat. Nos. 4,487,394 and 4,026,520, are capable of retracting and holding only one staple at a time. Furthermore, the size of most conventional extractors prohibits their use during laparoscopic surgery as the devices are too large to be inserted through a trocar. Also, trocars provide limited mobility for the movement of many instruments. Thus, when removing staples or clips during laparoscopic surgery, it is very time consuming to repeatedly insert conventional staple extractors through the trocar, grasp a single staple, remove it through the trocar, and repeat the process for each staple. It is desirable to reduce the time needed for this process, as well as any other step during surgery, to reduce the risk of infection to the patient.

Another problem posed by laparoscopic surgery in the removal of surgical staples is the visualization of applied staples. U.S. Pat. Nos. 3,643,851, 3,717,294 and 3,837,555 disclose devices for the stapling of skin. The staple used with these devices comprises two straight edges joined by a crossbar. The surgical staple disclosed in U.S. Pat. No. 4,014,492 has a more complex shape prior to insertion that assists in the gathering of the skin during emplacement. All of these staples would be difficult to locate through a trocar as the staple, when inserted into the skin or tissue, is shaped such that the exposed portion of the staple lies directly on the surface of the skin or tissue.

Specialized stapling systems have been developed for particular applications other than laparoscopic surgery. The staple, method, and extractor disclosed in U.S. Pat. No. 4,434,796, for example, is used to join bone tissues. In this system, extraction of the staples is accomplished one staple at a time, and, in fact, requires multiple extraction efforts for the removal of one staple.

OBJECTS OF THE INVENTION

One object of the present invention is to provide a surgical staple suitable for use in laparoscopic surgery.

It is another object of the invention is to provide a surgical staple that is easy to locate through a limited viewport, such as a trocar.

Another object of tile invention is to provide a surgical staple extractor that is suitable for use in laparoscopic surgery.

It is another object of tile invention is to provide a surgical staple extractor that is capable of removing and holding multiple staples.

SUMMARY OF THE INVENTION

The invention includes a laparoscopic surgical staple comprising first and second downwardly extending legs, and an extraction member formed to define a substantially closed hole and connected to the downwardly extending legs. The staple is visible through a limited viewport, such as a trocar, as the extraction member is above the body tissue and is made of a color which is in contrast to tile color of body tissue. The invention also includes a surgical staple extractor which includes a mechanism for grasping and pulling a surgical staple from body tissue, and which includes a hook located proximate the grasping mechanism. A method of applying a staple to body tissue of a patient by inserting the legs of a staple into the body tissue of the patient is disclosed. Also, methods for extracting multiple staples from internal body tissue are also disclosed. The extraction methods utilize staples together with a grasping and pulling mechanism and a hook capable of receiving multiple staples. The hook is positioned adjacent the internal body tissue to the surgical site where the staples are located, and each staple is extracted and placed on the hook so that multiple staples may be simultaneously removed from the surgical site. In laparoscopic surgery, these extraction methods limit the time required to remove multiple staples and reduce the risk of infection to the patient as the number of times that instruments are inserted into a trocar is minimal.

DETAILED DESCRIPTION

Figure 1A:
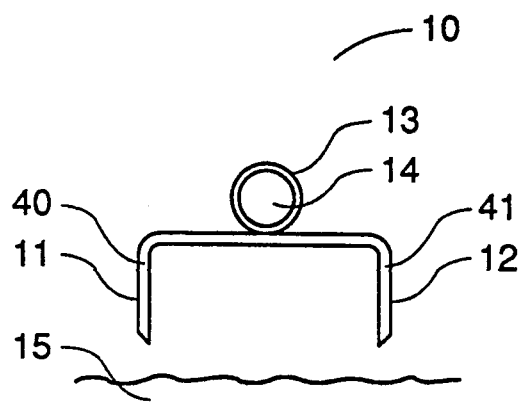
FIG. 1A shows a cross-sectional view of one embodiment of the surgical staple of the present invention.
Figure 1B:
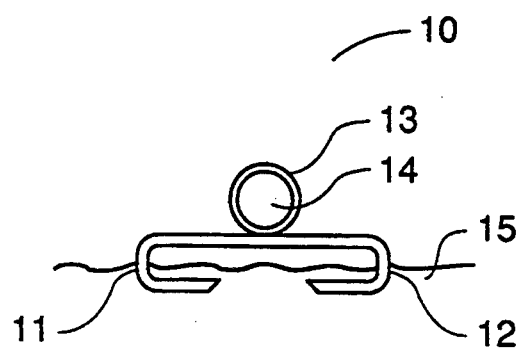
FIG. 1B shows a cross-sectional view of tile embodiment of FIG. 1A after it has been inserted into body tissue of a patient.

Referring now to FIG. 1A, there is shown a cross-sectional view of one embodiment of a surgical staple according to the present invention before the staple is inserted into a patient's body tissue. Laparoscopic surgical staple 10 comprises first 11 and second 12 downwardly extending legs connected to extraction member 13. The shape of extraction member 13 forms a substantially closed hole 14, and serves two purposes. First, extraction member 13 is visible when staple 10 is inserted into body tissue 15, as is shown in FIG. 1B, as extraction member 13 is above the surface of body tissue 15. Furthermore, extraction member 13 may be made of a color, such as green, that contrasts with the color of body tissue 15 or organs at the surgical site. Second, a hook (see FIG. 4) may be inserted into hole 14 to receive, or hold, staple 10. In this embodiment of staple 10, hole 14 is located between legs 11, 12 and is above upper ends 40, 41 of legs 11, 12.

Figure 1C:
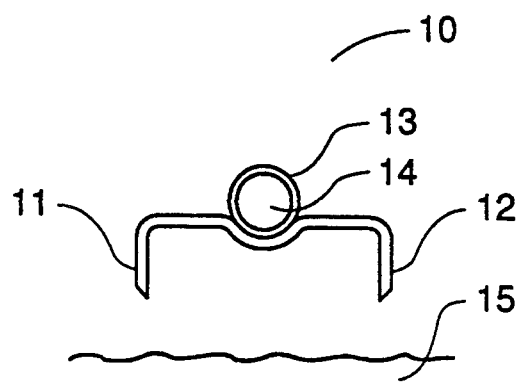
FIG. 1C shows a cross-sectional view of the embodiment of FIG. 1A after it has been removed from body tissue of a patient.

Referring to FIG. 1B, tile shape of staple 10 may be modified once it is inserted into body tissue 15. Specifically legs 11, 12 are, in part or in total, beneath the surface of tissue 15 and extraction member 13 is above the surface of tissue 15. As is shown in FIG. 1C, the shape of staple 10 may again be modified once it is removed from body tissue 15.

Figure 2A:
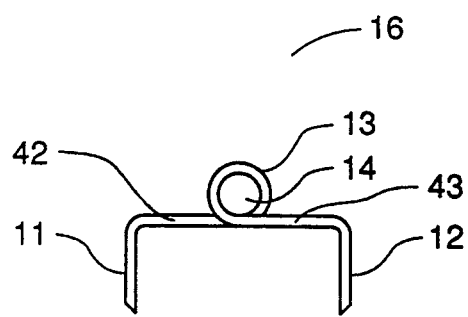
FIG. 2A shows a cross-sectional view of a second embodiment of the surgical staple of the present invention in which the staple is constructed from a single piece of material.
Figure 2B:
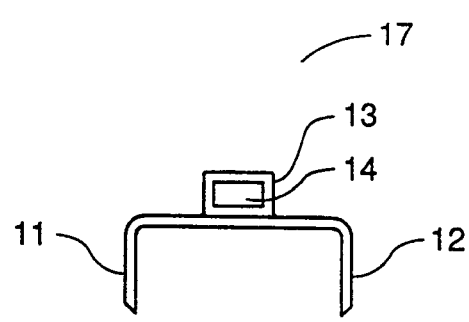
FIG. 2B shows a cross-sectional view of a third embodiment of the surgical staple of the present invention in which tile extraction member is rectangular in shape.
Figure 2C:
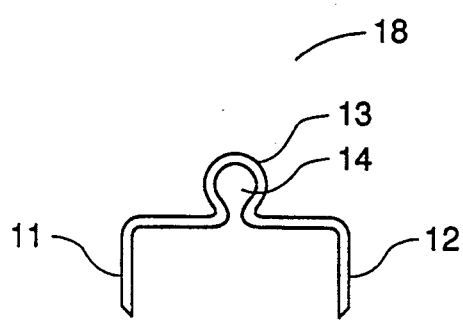
FIG. 2C shows a cross-sectional view of a fourth embodiment of the surgical staple of the present invention in which the extraction member defines a substantially closed hole.
Figure 2D:
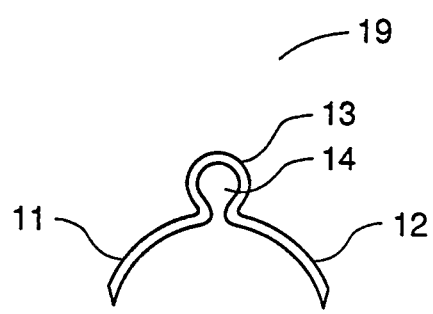
FIG. 2D shows a cross-sectional view of a fifth embodiment of the surgical staple of the present invention in which the legs are not parallel.

Referring to FIGS. 2A-D, other embodiments of the surgical staple of the present invention are illustrated. Staple 16 in FIG. 2A is comprised of a single piece of material and has a circular extraction member 13. In this embodiment, extraction member 13 includes first 42 and second 43 members which extend from tile portion of extraction member 13 defining hole 14 and which are connected to first 11 and second 12 legs, respectively. As Shown in FIG. 2153, staple 17 has a rectangular shaped extraction member 13 with legs 11, 12 parallel to each other. Staple 18, shown in FIG. 2C, has a circular extraction member 13 which forms substantially closed hole 14. Staple 19, shown in FIG. 2D, has legs 11, 12 which are not parallel to each other, but which do extend downward.

Each of the staples shown in FIG. 1A and FIGS. 2A-D may be applied using staple applicators well-known in the art capable of inserting legs 11, 12 into body tissue 15 of the patient. Also, conventional surgical staple extractors may be used to extract the laparoscopic surgical staples, and a hook device may be used to receive, or hold, the staples.

Figure 3:
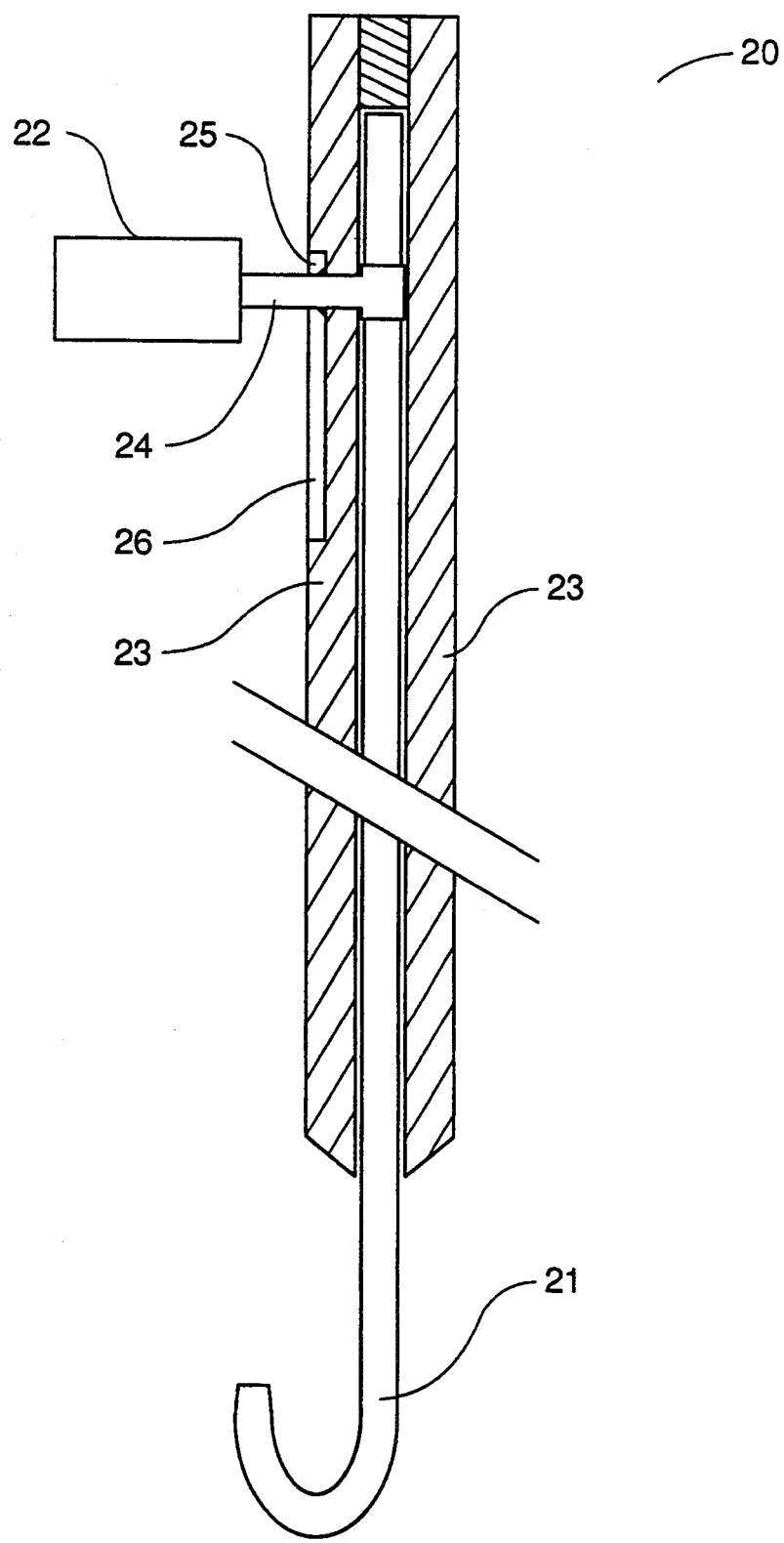
FIG. 3 shows a longitudinal cross-sectional view of one embodiment of the hook of the present invention used to extract staples.
Figure 4:
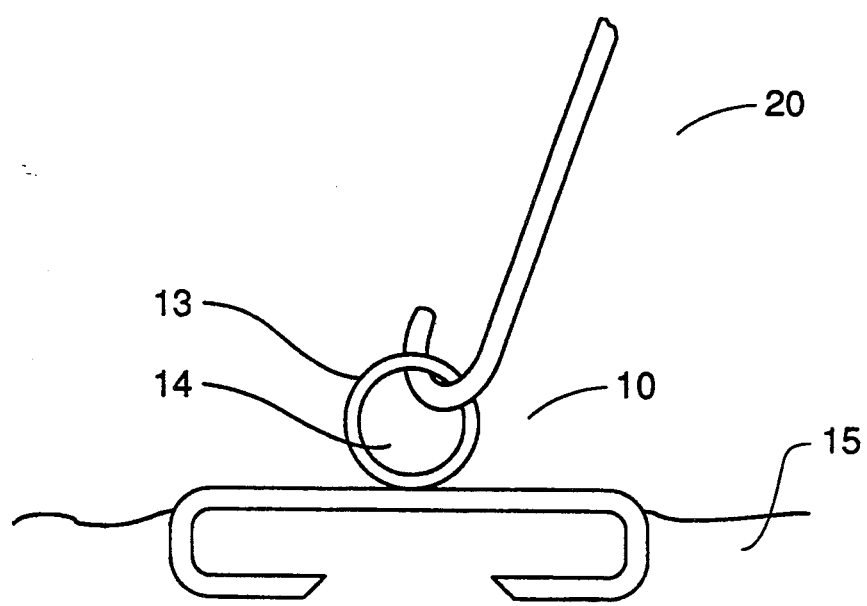
FIG. 4 shows a perspective view of the hook of the present invention inserted into tile hole defined by the extraction member of the surgical staple.

There is shown in FIG. 3 a longitudinal cross-sectional view of hook system 20 in accordance with the present invention which may be used to receive, or hold, staples 10, 16, 17, 18, 19. Hook 20 comprises J-hook 21 which, when used in laparoscopic surgery, is of a sufficient width and length to be placed through a trocar. As is shown in FIG. 4, J-hook 21 is inserted through substantially closed hole 14 of extraction member 13, and, therefore, must be of an appropriate size and shape to be placed through hole 14 and also be capable of holding more than one staple 10. Furthermore, hook 20 may be of a configuration which provides a means to adjust the position of J-hook 21. As is shown in FIG. 3, hook 20 includes housing 23 within which J-hook 21 is slidably movable. Handle 22 is attached to J-hook 21 by rod 24 which is slidable within channel 26 of housing 23 and which is stopped at the ends of channel 26 by stop 25 on rod 24. This, or a similar, simple construction may be used in laparoscopic surgery wherein J-hook 21 resides beneath tile patient's abdomen and the adjustment mechanism remains outside the abdomen, giving the surgeon control over the placement of J-hook 21 into hole 14 of extraction member 13.

Figure 5:
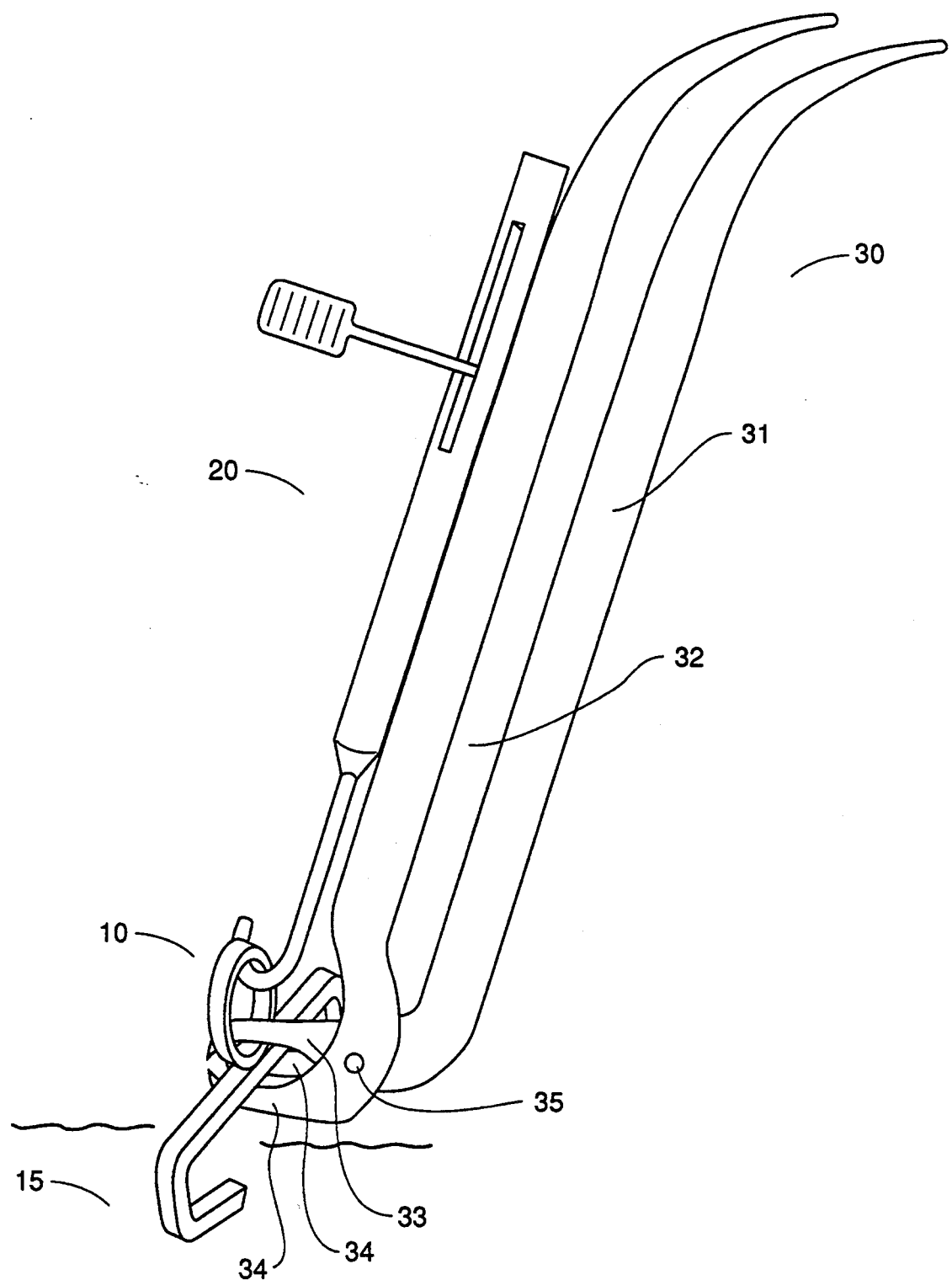
FIG. 5 shows a perspective view of a surgical staple extractor and the hook of the present invention positioned to extract and hook the surgical staple.

Referring now to FIG. 5, there is shown a modified conventional surgical staple extractor together with hook 20 in accordance with the present invention. Surgical staple extractor 30 includes handles 31, 32 which are pivotable about hinge 35. Handles 31, 32 may be adapted for use during laparoscopic surgery if they are of a sufficient length and of minimal width to permit a portion of surgical staple extractor 30 to be placed through a trocar. Jaws 33, 34, located at the distal end of surgical staple extractor 30, provide means of grasping and pulling staple 10 from body tissue 15. Located proximate to grasping means 33, 34 is hook 20 which operates in concert with jaws 33, 34 such that staple 10 to be extracted from body tissue 15 may, at an appropriate time, be hooked by hook 20 through hole 14, and such that extracted staple 10 remains hooked on hook 20 after staple 10 is extracted by jaws 33, 34. For use in a laparoscopic surgical site, hook 20 may be inserted through a different incision than the incision through which grasping means 33, 34 is inserted. However, to reduce the amount of risk of infection to the patient, it would be preferable to insert hook 20 and jaws 33, 34 through the same incision or trocar. Therefore, hook 20 may be included as a part of surgical staple extractor 30 as is illustrated in FIG. 5.

To remove staples from body tissue according to the present invention, two methods may be used. Each extraction method requires the use of laparoscopic staple 10, hook 20, and staple extractor 30. Initially, the applied staple is visualized. The green color of extraction member 13 assist in visualizing the staple, and helps ensure that no staples are inadvertently left in the patient. In the first method, hook 20 is inserted through hole 14 of extraction member 13. Staple 10 is then removed with staple extractor 30 while hook 20 continues to hold staple 10. After tile extraction of staple 10 with extractor 30, staple 10 remains to be held by hook 20. In the second method, staple 10 is removed with extractor 30 and then hook 20 is inserted into hole 14 of extraction member 13 before staple 10 is released from the grasp of extractor 30.

It will be appreciated by those of skill in tile art that the use of the staple, hook, and extractor of tile present invention allows multiple staples to be extracted in a single laparoscopic procedure. Multiple staples are removed without continually placing the extractor and/or hook into and out of the trocar(s). This reduces the risk of infection to the patient as well as the amount of time required to complete the procedure. Also, because the staple of the present invention is visible through a limited viewport, it is very feasible to use the staple together with tile methods of application and extraction disclosed herein in a laparoscopic surgical site.

I claim:

1. A method of applying a staple to body tissue of a patient, comprising the steps of:
   providing a laparoscopic surgical staple comprising
     first and second downwardly extending legs,
     an extraction member formed to define a substantially closed hole,
     the extraction member being connected to the downwardly extending legs; and inserting the legs of the staple into the body tissue of the patient such that the closed loop remain above the body tissue; and grasping the closed loop of the staple.

2. The method of claim 6 wherein the hole defined by the extraction member of the staple is circular.

3. The method of claim 1 wherein the legs and the extraction member of the staple are constructed from a single piece of material.

4. The method of claim 1 wherein the hole defined by the extraction member of the staple is between the legs.

5. The method of claim 1 wherein the legs of the staple have upper ends, and the portion of the extraction member defining the hole of the staple is above the upper ends of the legs.

6. The method of claim 1 wherein the extraction member of the staple includes first and second members extending from the portion of the extraction member defining the hole, the first and second members being connected to the first and second legs, respectively.

7. The method of claim 1 wherein the legs of the staple are parallel.

8. The method of claim 1 wherein the extraction member of the staple is made of a color which is sufficiently dissimilar, with respect to the color spectrum, from the color of human body tissue, such that the extraction member is distinguishable when placed next to body tissue.

9. A method of applying a staple to body tissue of a patient, the staple comprising first and second downwardly extending legs, and an extraction member formed to define a substantially closed hole, the extraction member being connected to the downwardly extending legs, the method comprising the steps of:
provoding a tube of sufficient inner diameter to allow the staple to pass therethrough;
making an incision in the patient;
inserting the tube through the incision;
inserting the staple through the tube to reach the patient's inner body tissue: and
inserting the legs of the staple into the body tissue.

10. The method of claim 9, wherein the tube comprises a trocar.

11. The method of claim 9, further comprising the step of providing a staple applicator sized to hold the staple, such that the staple applicator is inserted through the tube and such that the legs of the staple are inserted into the body by the staple applicator.

12. The method of claim 9, wherein the extraction member of the staple resides above the body tissue when the legs are inserted into the body tissue.

13. The method of claim 9, wherein the extraction member is mace of a color sufficiently differentiable from the body tissue such that the inserted staple is visible through the tube.

* * * * *